United States Patent [19]

Meade et al.

[11] Patent Number: 4,873,316

[45] Date of Patent: Oct. 10, 1989

[54] ISOLATION OF EXOGENOUS RECOMBINANT PROTEINS FROM THE MILK OF TRANSGENIC MAMMALS

[75] Inventors: Harry Meade, Newton, Mass.; Nils Lonberg, New York, N.Y.

[73] Assignee: Biogen, Inc., Cambridge, Mass.

[21] Appl. No.: 65,994

[22] Filed: Jun. 23, 1987

[51] Int. Cl.$^4$ .................... C07K 3/02; C07K 3/12; C07K 3/18; C12N 15/00

[52] U.S. Cl. ................... 530/412; 530/360; 530/361; 530/833; 530/832; 530/416; 530/417; 530/418; 435/68; 435/172.1; 435/172.3; 435/240.2; 935/53; 935/55; 935/70; 935/111; 800/1; 536/27; 536/28; 536/29

[58] Field of Search ............ 435/68, 172.1, 172.3, 435/226, 240.2; 530/832, 833, 412, 360, 361, 303; 800/1; 935/53, 55, 70; 536/27, 28, 29

[56] References Cited

U.S. PATENT DOCUMENTS

| | | | |
|---|---|---|---|
| 4,018,752 | 4/1977 | Bühler et al. | 530/382 |
| 4,229,342 | 10/1980 | Mirabel | 530/382 |
| 4,376,072 | 3/1983 | Connolly | 530/382 |
| 4,396,601 | 8/1983 | Salser et al. | 435/172.3 |
| 4,462,932 | 7/1984 | Lonergan | 530/382 |
| 4,644,056 | 2/1987 | Kothe et al. | 530/382 |
| 4,736,866 | 4/1988 | Leder et al. | |

FOREIGN PATENT DOCUMENTS

| | | | |
|---|---|---|---|
| 0117059 | 8/1984 | European Pat. Off. | 435/172.3 |
| 0247494 | 12/1987 | | |
| 0264166 | 4/1988 | | |
| WO88/00239 | 1/1988 | PCT Int'l Appl. | |
| WO88/01648 | 3/1988 | PCT Int'l Appl. | |

OTHER PUBLICATIONS

Gordon et al., Bio/Technology, 5, 1183–7, (Nov. 1987).
Lovell-Badge, Nature, 315, 628–629, (1985).
Hammer et al., Nature, 415, 680–683, (Jun. 20, 1985).
Garcia et al., Mol. Cell. Biol., 6(6), 1974–82, (1986).
Palmiter et al., J. Cell. Bioch., 8B, p. 25, Ab. #0890, (1984).
Fisher et al., J. B. C., 260 (20), 11223–11230, 1985.
Andres et al., Chem. Abs. 106(17):133024q, 1987 (for PNAS USA, 84(5), 1299–303, May 1987).
Ross et al., P.N.A.S. (USA), 82, 5880–84, 1985.
Brinster et al., Cell, 27, 223–31, Nov. 1981.

*Primary Examiner*—Margaret Moskowitz
*Assistant Examiner*—Jeff P. Kushan
*Attorney, Agent, or Firm*—James F. Haley, Jr.; Teresa L. Solomon

[57] ABSTRACT

This invention relates to the production of recombinant proteins in mammals' milk. Particularly, this invention relates to an expression system comprising the mammal's casein promoter which when transgenically incorporated into a mammal permits the female species of that mammal to produce the desired recombinant protein in or along with its milk. This invention also relates to the transgenic mammal that produces the desired recombinant product in its milk.

3 Claims, 1 Drawing Sheet

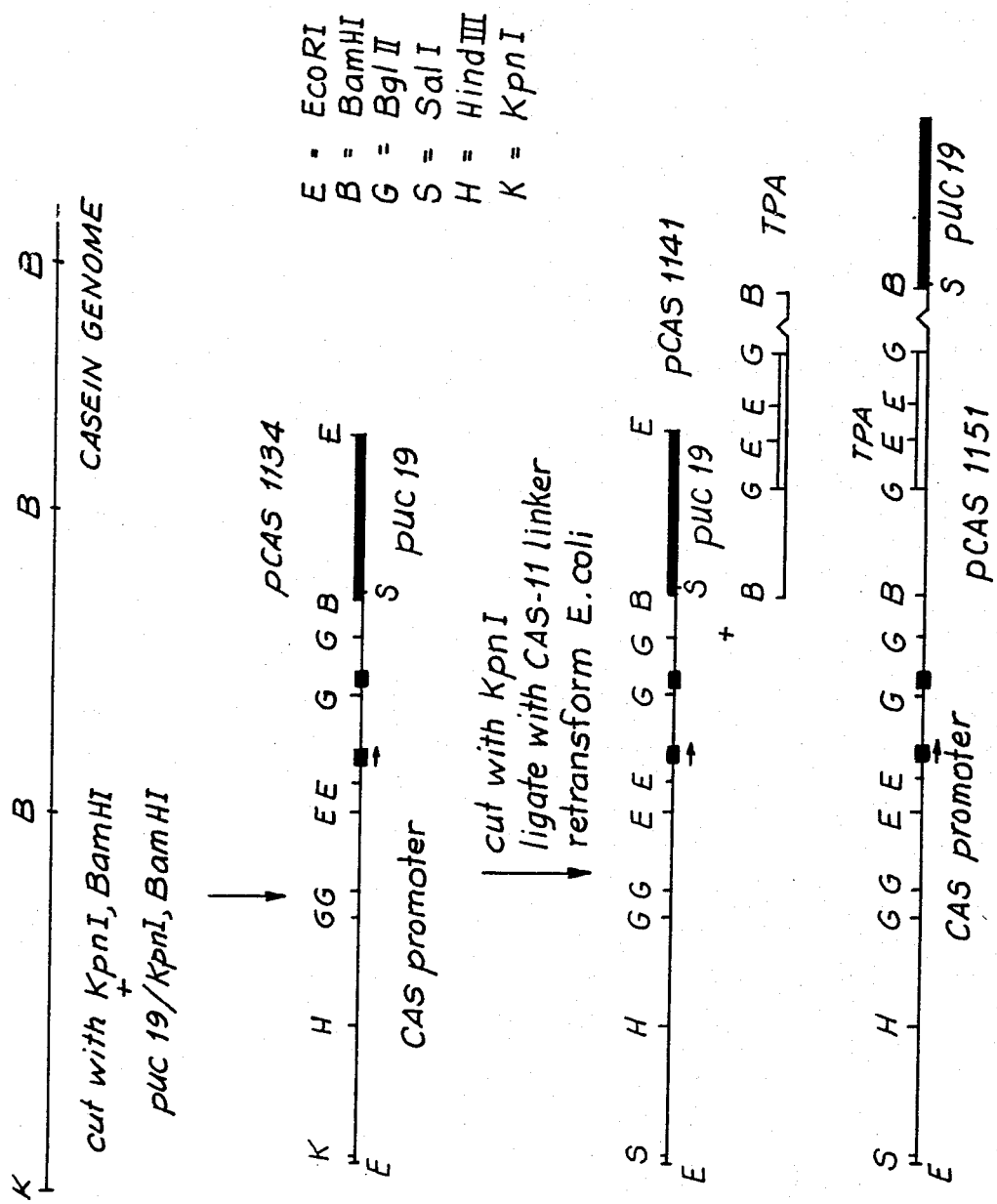

ISOLATION OF EXOGENOUS RECOMBINANT PROTEINS FROM THE MILK OF TRANSGENIC MAMMALS

TECHNICAL FIELD OF INVENTION

This invention relates to the production of recombinant proteins in mammals' milk. Particularly, this invention relates to an expression system which comprises at least a milk-specific protein promoter operatively linked to a DNA sequence coding for a signal peptide and a desired recombinant protein product. When such a system is transgenically incorporated into a mammal, the recombinant protein is expressed in the milk of the lactating transgenic mammal. This invention also relates to the transgenic mammal that produces the desired recombinant product in its milk. Recombinant products produced by the expression systems and transgenically altered mammals of this invention can be produced at significantly less cost than by conventional recombinant protein production techniques.

BACKGROUND ART

Recombinant DNA technology has enabled the cloning and expression of genes encoding medically and agriculturally important proteins and glycoproteins. Such products include, for example, insulin, growth hormone, growth hormone releasing factor, somatostatin, tissue plasminogen activator, tumor necrosis factor, lipocortin, coagulation factors VIII and IX, the interferons, colony stimulating factor, the interleukins and urokinase.

Many of these important proteins, however, are large (molecular weights in excess of 30Kd), secreted, require sulfhydryl bonds to maintain proper folding, are glycosylated and are sensitive to proteases. As a result, the recombinant production of such products in prokaryotic cells has proven to be less than satisfactory because the desired recombinant proteins are incorrectly processed, lack proper glycosylation or are improperly folded. Accordingly, resort has been had to the production of those recombinant proteins in cultured eukaryotic cells. This technique has proven to be both expensive and often unreliable due the variability of cell culture methods. For example, average yields are 10 mg of recombinant protein per liter of culture media, with the resulting cost typically for exceeding $1,000 per gram of recombinant protein. Accordingly, resort has been had to the production of those recombinant proteins in cultured eukaryotic cells.

DISCLOSURE OF THE INVENTION

The present invention solves such problems by providing an efficient means of producing large quantities of recombinant protein products in the milk of transgenically altered mammals. According to this invention, a DNA sequence coding for a desired protein is operatively linked in an expression system to a milk-specific protein promoter, or any promoter sequence specifically activated in mammary tissue, through a DNA sequence coding for a signal peptide that permits secretion and maturation of the desired protein in the mammary tissue. More preferably, the expression system also includes a 3' untranslated region downstream of the DNA sequence coding for the desired recombinant protein. This untranslated region may stabilize the rDNA transcript of the expression system. Optionally, the expression system also includes a 5' untranslated region upstream of the DNA sequence coding for the signal peptide.

The expression system is transgenically introduced into a host genome by standard transgenic techniques. As a result, one or more copies of the construct or system becomes incorporated into the genome of the transgenic mammal. The presence of the expression system will permit the female species of the mammal to produce and to secrete the recombinant protein product, into or along with its milk. Such method permits the low cost, high level production of the desired proteins.

BRIEF DESCRIPTION OF THE DRAWINGS

FIG. 1 depicts the construction of a plasmid of this invention, pCAS 1151.

DEFINITIONS

As used in this application and claims, the terms recombinant protein and operatively linked have the following definitions:

Operatively linked—the linking of a milk-specific promoter or a promoter specifically activated in mammary tissue to a DNA sequence coding for a desired protein so as to permit and control expression of that DNA sequence and production of that protein.

Recombinant protein—a protein or peptide coded for by a DNA sequence which is not endogeneous to the native genome of the mammal in whose milk it is produced in accordance with this invention or a protein or peptide coded for by a DNA sequence which if endogeneous to the native genome of the mammal in whose milk it is produced does not lead to the production of that protein or peptide in its milk at the same level that the transgenic mammal of this invention produces that protein in its milk.

DETAILED DESCRIPTION OF THE INVENTION

This invention relates to processes, DNA sequences, compositions of matter and transgenic mammals for the production of recombinant proteins More specifically, this invention relates to the transgenic incorporation of one or more copies of a construct comprising a milk-specific protein promoter or any promoter sequence specifically activated in mammary tissue, operatively linked to a DNA sequence coding for a desired recombinant protein through a DNA sequence coding for a signal peptide that permits the secretion and maturation of the desired recombinant protein in the mammary tissue. The construct is transgenically incorporated into mammalian embryos and the recombinant protein product is subsequently expressed and secreted into or along with the milk of the lactating transgenic mammal.

Any mammal may be usefully employed in this invention. Preferably, mammals that produce large volumes of milk and have long lactating periods are preferred. Preferred mammals are cows, sheep, goats, mice, oxen, camels and pigs. Of course, each of these mammals may not be as effective as the others with respect to any given expression sequence of this invention. For example, a particular milk-specific promoter or signal sequence may be more effective in one mammal than in others However, one of skill in the art may easily make such choices by following the teachings of this invention.

Among the milk-specific protein promoters useful in the various embodiments of this invention are the casein promoters and the beta lactoglobulin promoter. The casein promoters may, for example, be selected from an alpha casein promoter, a beta casein promoter or a kappa casein promoter. Preferably, the casein promoter is of bovine origin and is an alpha S-1 casein promoter. Among the promoters that are specifically activated in mammary tissue and are thus useful in accordance with this invention is the long terminal repeat (LTR) promoter of the mouse mammary tumor virus (MMTV) The milk-specific protein promoter or the promoters that are specifically activated in mammary tissue may be derived from either cDNA or genomic sequences. Preferably, they are genomic in origin.

Among the signal peptides that are useful in accordance with this invention are milk-specific signal peptides or other signal peptides useful in the secretion and maturation of eukaryotic and prokaryotic proteins. Preferably, the signal peptide is selected from milk-specific signal peptides or the signal peptide of the desired recombinant protein product, if any. Most preferably, the milk-specific signal peptide is related to the milk-specific promoter used in the expression system of this invention. The size of the signal peptide is not critical for this invention. All that is required is that the peptide be of a sufficient size to effect secretion and maturation of the desired recombinant protein in the mammary tissue where it is expressed.

Among the protein products which may be produced by the processes of this invention include, for example, coagulation factors VIII and IX, human or animal serum albumin, tissue plasminogen activator (TPA), urokinase, alpha-1 antitrypsin, animal growth hormones, Mullerian Inhibiting Substance (MIS), cell surface proteins, insulin, interferons, interleukins, milk lipases, antiviral proteins, peptide hormones, immunoglobulins, lipocortins and other recombinant protein products.

The desired recombinant protein may be produced as a fused protein containing amino acids in addition to those of the desired or native protein. For example, the desired recombinant protein of this invention may be produced as part of a larger recombinant protein in order to stabilize the desired protein or to make its purification from milk easier and faster The fusion is then broken and the desired protein isolated. The desired recombinant protein may alternatively be produced as a fragment or derivative of native protein or it may be produced having an amino acid sequence similar to the native protein. Each of these alternatives is readily produced by merely choosing the correct DNA sequence.

Preferably, the expression system or construct of this invention also includes a 3' untranslated region downstream of the DNA sequence coding for the desired recombinant protein. This region apparently stabilizes the RNA transcript of the expression system and thus increases the yield of desired protein from the expression system. Among the 3' untranslated regions useful in the constructs of this invention are sequences that provide a poly A signal. Such sequences may be derived, e.g., from the SV40 small t antigen, the casein 3' untranslated region or other 3' untranslated sequences well known in the art. Preferably, the 3' untranslated region is derived from a milk specific protein. The length of the 3' untranslated region is not critical but the stabilizing effect of its poly A transcript appears important in stabilizing the RNA of the expression sequence.

Optionally, the expression control sequences of this invention also include a 5' untranslated region between the promoter and the DNA sequence encoding the signal peptide. Such untranslated regions are preferably related to the promoter. However, they may be derived from other synthetic, semi-synthetic and natural sources. Again their specific length is not critical, however, they appear to be useful in improving the level of expression.

The above-described expression systems may be prepared using methods well known in the art. For example, various ligation techniques employing conventional linkers, restriction sites etc. may be used to good effect. Preferably, the expression systems of this invention are prepared as part of larger plasmids Such preparation allows the cloning and selection of the correct constructions in an efficient manner as is well known in the art. Most preferably, the expression systems of this invention are located between convenient restriction sites on the plasmid so that they can be easily isolated from the remaining plasmid sequences for incorporation into the desired mammal.

After such isolation and purification, the expression systems or constructs of this invention are added to the gene pool of the mammal which is to be transgenically altered. For example, one or several copies of the construct may be incorporated into the genome of a mammalian embryo by standard transgenic techniques.

One technique for transgenically altering a mammal is to microinject the construct into the pronuclei of the fertilized mammalian egg(s) to cause one or more copies of the construct to be retained in the cells of the developing mammal(s). Usually, at least 40% of the mammals developing from the injected eggs contain at least one copy of the cloned construct in somatic tissues and these "transgenic mammals" usually transmit the gene through the germ line to the next generation. The progeny of the transgenically manipulated embryos may be tested for the presence of the construct by Southern blot analysis of a segment of tissue. If one or more copies of the exogenous cloned construct remains stably integrated into the genome of such transgenic embryos, it is possible to establish permanent transgenic mammal lines carrying the transgenically added construct.

The litters of transgenically altered mammals may be assayed after birth for the incorporation of the construct into the genome of the offspring. Preferably, this assay is accomplished by hybridizing a probe corresponding to the DNA sequence coding for the desired recombinant protein product or a segment thereof onto chromosomal material from the progeny. Those mammalian progeny found to contain at least one copy of the construct in their genome are grown to maturity. The female species of these progeny will produce the desired protein in or along with their milk. Alternatively, the transgenic mammals may be bred to produce other transgenic progeny useful in producing the desired proteins in their milk.

EXAMPLES

EXAMPLE 1

Bovine Alpha S-1 Casein

We cloned bovine alpha S-1 casein with a cosmid library of calf thymus DNA in the cosmid vector HC79 (from Boehringer Mannheim) as described by B. Hohn and J. Collins, *Gene*, 11, pp. 291–298 (1980). The thymus was obtained from a slaughterhouse and the DNA isolated by standard techniques well known in the art (T. Maniatis et al., "Molecular Cloning: A Laboratory Manual", Cold Spring Harbor Laboratory at p. 271 (1982)). We isolated the cosmid library using standard techniques (F. Grosveld et al., *Gene*, 13, pp. 227–231 (1981)). We partially digested the calf thymus DNA with Sau3A (New England Bio Labs) and ran it on a salt gradient to enrich for 30 to 40 kb fragments. The partially digested DNA fragments were then ligated with BamHI digested HC79 cosmid vector, followed by in vitro packaging by lambda extracts (Amersham) following the manufacturer's recommendation. The in vitro packaged material was then used to infect the *E.coli* K-12 strain HB101 followed by selection on LB plates containing 50 μg/ml of Ampicillin [Sigma].

We screened this library using a 45 base pair oligonucleotide probe: CAS-1. This CAS-1 sequence, 5' CATGGCTTGATCTTCAGTTGATTCACTC-CCAATATCCTTGCTCAG 3', was obtained from a partial cDNA sequence of alpha S-1 casein as described by I. M. Willis et al., *DNA*, 1, pp. 375–386 (1982). This sequence corresponds to amino acids 20–35 of mature bovine casein.

As a result of this screening, we isolated three cosmids (C9, D4 and E1). Partial subcloning of C9 and sequencing demonstrated that the cosmid represented a portion of the genomic sequence of the alpha S-1 casein gene.

We then synthesized several oligonucleotide probes corresponding to regions of the casein cDNA, based on published sequences [A. F. Stewart et al. *Nucleic Acids Res.*, 12, p. 3895 (1984); M. Nagao et al., *Agric. Biol. Chem.*, 48, pp. 1663–1667 (1984)]. Restriction mapping and Southern blot analysis [E. Southern, J. Mol. Biol., 98, p. 503 (1975)] established that cosmids D4 and E1 contained the structural gene and 9kb of upstream or 5' flanking sequences. The C9 cosmid contained the casein structural gene and 8kb of downstream or 3' sequences (see FIG. 1). We sequenced the cosmids E1 and D4 in the region corresponding to the transcriptional start of the casein structural sequence and determined that the sequence corresponded to that of the same region as described by L. L. Yu-Lee et al., *Nucleic Acid Res.*, 14, pp. 1883–1902 (1986).

We believe that the controlling region of Alpha S-1 casein is located upstream of the start of transcription. We have established after sequencing that there is a 40bp Exon I and that the signal sequence of CAS along with the sequences which encode the first two amino acids of mature CAS—arginine and glutamine —are found in Exon II.

We constructed the CAS promoter plasmid as follows: The genomic map of FIG. 1 shows that the control or promoter region along with Exons I and II may be cloned as a 9kb KpnI-BamHI fragment. Accordingly, we digested the E1 cosmid with KpnI and BamHI, then ligated it to pUC19 (Bethesda Research Labs) which had been previously cut with KpnI and BamHI. The resulting plasmid pCAS 1134 (see FIG. 1) contained the CAS promoter and signal sequence with a BamHI site suitable for cloning.

In order to allow the genomic construct to function in a eukaryotic host, i.e., to carry out transgenic work in which DNA is injected into the pronucleus, the prokaryotic sequences must first be removed. One method employed to remove prokaryotic sequences was to modify the pCAS 1134 so that the SalI sites flank the eukaryotic DNA. The KpnI site located upstream of the CAS promoter was changed to a SalI site using the CAS-11 linker 5' GGT CGA CCG TAC 3' which was ligated into the plasmid following digestion with KpnI. The resulting plasmid, pCAS 1141 (see FIG. I) contained SalI sites flanking the CAS promoter and the BamHI cloning site.

EXAMPLE 2

Construction of the Cas-Recombinant Product Construct

One recombinant protein that can be produced by the process of this invention is tissue plasminogen activator or TPA. As demonstrated below, the casein signal peptide was used to direct secretion of TPA from the mammary glands of transgenic mice carrying a construct according to this invention. In this construct, the nucleotide sequence of the casein signal peptide was fused to the sequence of mature TPA by RNA processing. The sequence of TPA has been described in D. Pennica et al., Nature, 301, pp. 214–221 (1983). In the TPA gene, as in the CAS gene, there is a BamHI site in Intron II which separates the signal peptide from the mature sequence [R. Fisher et al., *J. Biol. Chem.*, 260, pp. 11223–1130 (1985)]. The cDNA of TPA shows the BglII site in Exon III at amino acid #3 of mature TPA.

We subcloned a 1.7kb fragment from the genomic clone of TPA [R. Fisher et al., supra] using BamHI-BglII. The 1.7kb fragment contained a portion of Intron II, the 3' splice acceptor site and Exon III up to the BglII site. This 1.7kb fragment was used to replace the TPA signal sequence found in the cDNA clone of TPA to provide a BamHI cassette. As shown in Example 1, there is a BamHI site located in Intron II which separates the sequence for the casein signal peptide from the sequence of the mature protein. The CAS promoter plasmid pCAS1141 was digested with BamHI and the BamHI cassette containing TPA was ligated into the digested plasmid, as shown in FIG. 1, to yield plasmid pCAS1151, which contains the CAS promoter upstream of the cDNA sequence of TPA. This construct allows the TPA structural sequences to accept the casein signal sequence by RNA processing.

We then isolated the DNA for use to transgenically alter mammals. We digested the pCAS1151 DNA to completion with SalI. Following electrophoresis in 1% agarose TBE [Maniatis et al., supra] the 13kb fragment corresponding to the eukaryotic sequences was cut out of the gel and the DNA electroeluted. We then centrifuged the DNA overnight in an equilibrium CsCl gradient. We removed the DNA band and dialyzed extensively against the buffer TNE (5 mM Tris, pH 7.4, 5 mM NaCl, and 0.1 mM EDTA, pH 8).

EXAMPLE 3

Transgenic Incorporation of the Construct Into Mice

The procedure for transgenic incorporation of the desired genetic information into the developing mouse embryo is established in the art [B. Hogan et al., "Manipulating The Mouse Embryo: A Laboratory Manual" Cold Spring Harbor Laboratory (1986)]. We used an F1 generation (Sloan Kettering) cross between C57B1 and CB6 (Jackson Laboratories). Six week old females were superovulated by injection of Gestile (pregnant mare serum) followed by human chorionic gonadotropin two days later. The treated females were bred with C57B1 stud males 24 hours later. The preimplantation fertilized embryos were removed within 12 hours following mating for microinjection with DNA and implantation into pseudopregnant females.

We injected the construct by first digesting the cumulus cells surrounding the egg with Hyaluronidase. The construct was injected into the pronucleus of the embryo until it swelled 30% to 50% in size. We then implanted the injected embryos (262) into the oviducts of pseudopregnant F1 females. Of 262 embryos injected and implanted, twenty three live pups were born. Tail blots of these were done and probed with nick translated pCAS1151 DNA, demonstrating that five of them contained the CAS sequence. Two of the female G0 progeny were cross bred to males at six weeks to produce a G1 generation. We tested the progeny of these matings for pCAS1151 sequences by tail blots. We then bred and milked the female obtained following parturition. Those female mice that carried the pCAS1151 DNA sequence produced TPA in their milk while the controls did not.

We mated transgenic male G0 mice with control females. We tested the G1 progeny by tail blotting and raised and bred for milking, females which carry the pCAS1152 sequence. The G1 progeny produced 0.2-0.5 μg/ml of TPA in their milk. We next crossed these females with a wild type F1. The progeny that carried the pCAS1151 DNA sequence produced the same TPA levels, while those that did not carry the sequence produced no TPA in their milk.

EXAMPLE 4

Transgenic Incorporation of the Human TPA Sequence into Large Mammals

After at least one prior estrus period, sheep are superovulated before becoming embryo donors. More specifically, at about day 10 of the estrus cycle, each sheep is implanted with a progestagen-impregnated vaginal sponge (each sponge containing 60 mg 6 alpha-methyl-17 alpha-acetoxy progesterone). The sponge remains implanted for 12 days. Three days before the sponge is removed and until the day following removal, each animal receives a gonadotropin treatment, consisting of administration of 2.5 mg porcine follicle stimulating hormone by intramuscular injection twice daily. At the onset of estrus, the sheep are either hand mated to fertile rams or inseminated in utero with 0.2 ml per horn of washed ram semen. Within 72 hours of sponge removal, one cell fertilized embryos and cleaved embryos are surgically collected from the reproductive tracks of anesthetized sheep by retrograde flushing with about 6 ml Ham's F-10 medium containing 10% heat-inactivated fetal calf serum from the utero-tubal junction through the cannulated infundibular end of each oviduct. The flushings are collected and embryos removed under a dissecting microscope.

The embryos are then transferred to fresh Ham's F-10 containing 10% fetal calf serum and transferred to the stage of an inverted microscope equipped with micromanipulators. Each embryos is then microinjected with a plurality of a construct, such as pCAS to 1151, according to the process set forth in R. L. Brinster et al., Cell, 27, pp. 223-231 (1981). The embryos are then aspirated into a glass pipet tip with 10 ml Hams F-10 and expelled 1-3 cm into the fimbriated end of the oviduct in synchronized recipient sheep. These sheep then are permitted to gestate for the appropriate time and their progany are tested for incorporation of a DNA sequence coding for TPA. The female species of these transgenic offspring produce TPA in their milk.

A construct according to this invention containing plasmid pCAS 1151 is exemplified by a culture deposited in the American Type Culture Collection, Rockville, Md., on June 23, 1987 and there identified as LE392/pCAS1151, wherein pCAS1151 is in E. coli K12. It has been assigned accession number ATCC 67450.

While we have hereinbefore presented a number of embodiments of our invention, it is apparent that our basic construction may be altered to provide other embodiments which utilize the processes and compositions of this invention. Therefore, it will be appreciated that the scope of this invention is to be defined by the claims appended hereto, rather than the specific embodiments which have been presented hereinbefore by way of example.

We claim:

1. A process for the production and secretion into mammal's milk of an exogenous recombinate protein comprising the steps of:
    a. producing milk in a transgenic mammal characterized by an expression system comprising a casein promoter operatively linked to an exogenous DNA sequence coding for the recombinant protein through a DNA sequence coding for a signal peptide effective in secreting and maturing the recombinant protein in mammary tissue;
    b. collecting the milk; and
    c. isolating the exogenous recombinant protein from the milk.

2. The process according to claim 1, wherein said expression system also includes a 3' untranslated region downstream of the DNA sequence coding for the recombinant protein.

3. The process according to claim 1, wherein said expression system also includes a 5' untranslated region between said promoter and the DNA sequence coding for the signal peptide.

* * * * *

UNITED STATES PATENT AND TRADEMARK OFFICE
CERTIFICATE OF CORRECTION

PATENT NO. : 4,873,316

DATED : October 10. 1989

INVENTOR(S) : Harry Meade and Nils Lonberg

It is certified that error appears in the above-identified patent and that said Letters Patent is hereby corrected as shown below:

Col. 1, line 1, insert "This invention was supported by United States Federal Government funding. The Government has certain rights in the invention."

Signed and Sealed this

Sixteenth Day of March, 1993

Attest:

STEPHEN G. KUNIN

*Attesting Officer*    Acting Commissioner of Patents and Trademarks